United States Patent [19]

Udaka et al.

[11] Patent Number: 4,507,282

[45] Date of Patent: Mar. 26, 1985

[54] HIGH MOLECULAR WEIGHT ANTITUMOR ANTIBIOTIC AN-7D

[75] Inventors: Shigezo Udaka; Shigeyoshi Miyashiro, both of Nagoya; Eikou Shimizu, Kawasaki; Tsuyoshi Shiio, Kamakura, all of Japan

[73] Assignee: Ajinomoto Co., Inc., Tokyo, Japan

[21] Appl. No.: 502,531

[22] Filed: Jun. 10, 1983

Related U.S. Application Data

[63] Continuation-in-part of Ser. No. 387,253, Jun. 10, 1982, abandoned.

[30] Foreign Application Priority Data

Jun. 10, 1981 [JP] Japan ................... 56-89316

[51] Int. Cl.$^3$ .............................................. A61K 35/74
[52] U.S. Cl. .................................................. 424/117
[58] Field of Search ......................... 424/117; 435/169

Primary Examiner—Jerome D. Goldberg
Attorney, Agent, or Firm—Oblon, Fisher, Spivak, McClelland & Maier

[57] ABSTRACT

A high molecular weight peptide antibiotic designated as AN-7D which is effective as an agent.

1 Claim, 2 Drawing Figures

HIGH MOLECULAR WEIGHT ANTITUMOR ANTIBIOTIC AN-7D

This application is a continuation-in-part of application Ser. No. 387,253, filed June 10, 1982, now abandoned.

BACKGROUND OF THE INVENTION

1. Field of the Invention

The present invention relates to a high molecular weight antitumor antibiotic which has a broad antitumor activity against the cells of mouse leukemia and which exhibit very low toxicity.

2. Description of the Prior Art

Many high molecular weight peptides produced by members of the group Actinomycetes have been known to exhibit antibiotic activity. Among known agents, high molecular weight antibiotics which exhibit antimicrobial activity are shown in Table 1.

TABLE 1

Known High Molecular Weight Antibiotics

| Name | Reference |
|---|---|
| Carcinocidin | Y. Harada, T. Nara and F. Okamoto: J. Antibiotics, serA 9(1), 6(1956). |
| Melanomycin | R. Sugawara, A. Matsunae and T. Hata: J. Antibiotics, serA 10(4), 133(1956). |
| A-280 | Y. Sekizawa, S. Inouye and K. Kagino: J. Antibiotics, serA 15(6), 236(1962). |
| Iyomycin complex | S. Nomura, H. Yamamoto, A. Matsumae and T. Hata: J. Antibiotics, serA 17(3), 104(1964). |
| Plurallin | H. Ogawara, K. Maeda, K. Nitta, Y. Okami: J. Antibiotics, serA 19(1), 1(1966). |
| Actinoxanthin | Khokholv, A.S. et al: J. Antibiotics, 22, 541(1969). |
| Neocarzinostatin | Ishida, N., K. Mizazaki, K. Kumagai & M. Rikimaru: J. Antibiotics, serA 18(2), 68(1965). |
| Macromomycin | Chimura, H., M. Ishizuka, S. Hori, K. Kimura, J. Iwanaga, T. Takeuchi and H. Umezawa: J. Antibiotics, 21, 44(1968). |
| Sporamycin | Umeyawa H., K. Komiyama, H. Takesima, J. Awaga & S. Omura: J. Antibiotics, 29, 1249(1976). |

Of these known antibiotics, Neocarzinostatin (hereinafter referred to as NCS) is a commercial product and is available on the market as a cancer chemotherapeutic agent. However, many of the remaining compounds are not of commercial importance because of their toxic properties and because of their comparatively low effectiveness. A need, therefore continues to exist for high molecular weight antibiotics which exhibit excellent activity while also exhibiting substantially reduced toxicity.

SUMMARY OF THE INVENTION

Accordingly, one object of the present invntion is to provide an agent which exhibits broad activity without exhibiting toxicity.

Briefly, this object and other objects of the present invention as hereinafter will become more readily apparent can be attained by a high molecular weight antibiotic AN-7D which exhibits activity.

DETAILED DESCRIPTION OF THE PREFERRED EMBODIMENTS

High molecular weight antibiotic AN-7D which exhibits broad activity against mouse luekemia with extremely low toxicity has been found in, and obtained from, a culture broth of Actinomyetes belonging to the genus Streptomyces.

Figure 1:
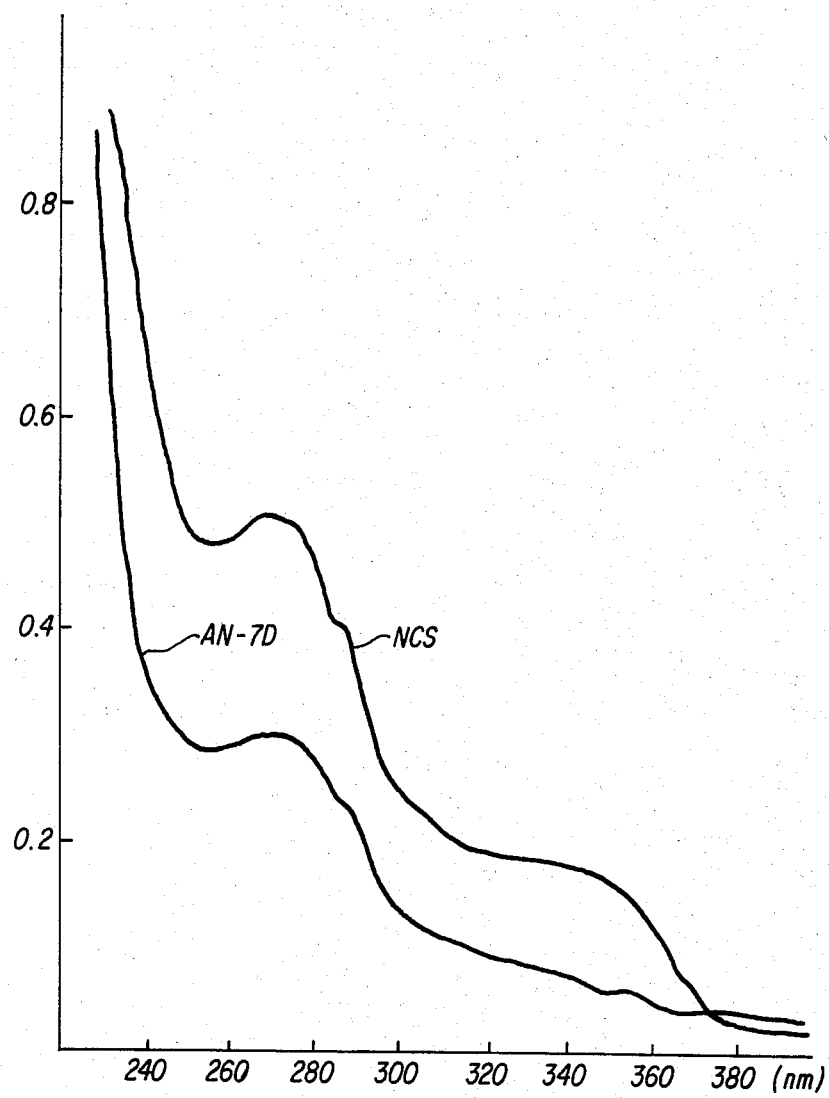
Figure 2:
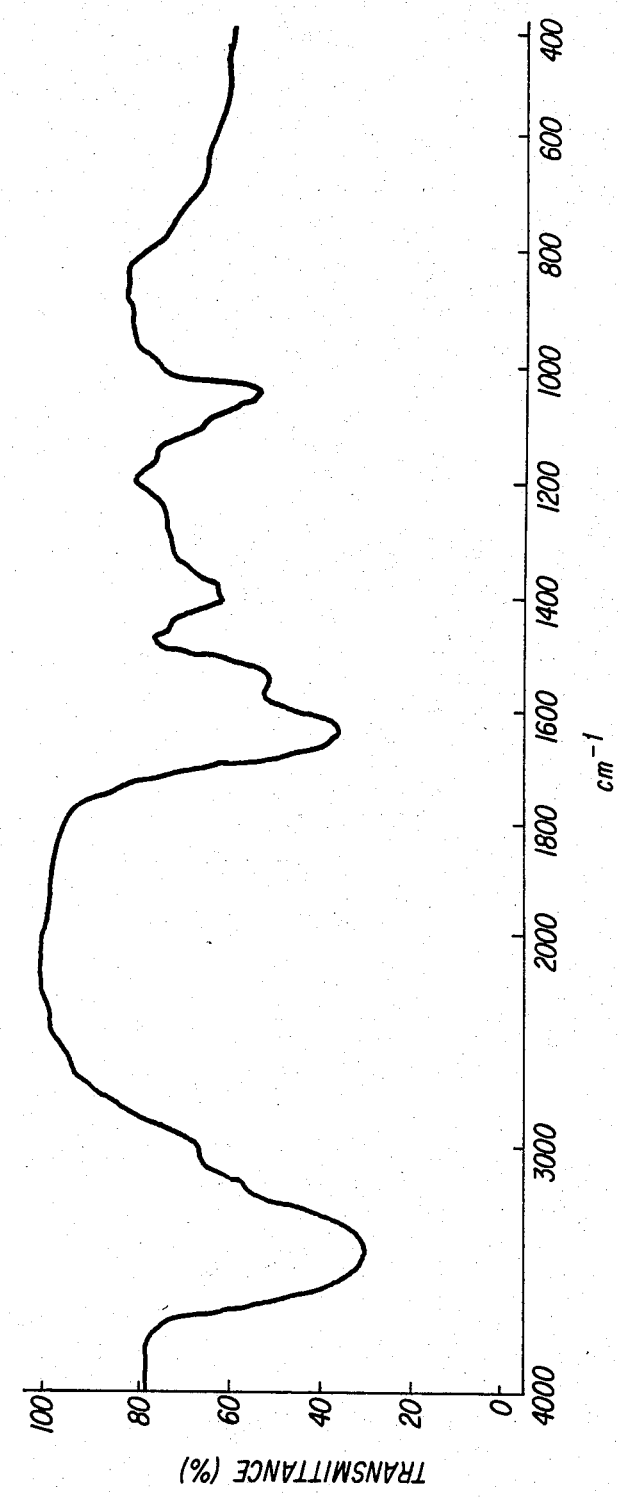

AN-7D obtained from a culture broth and purified by a series of conventional purification techniques which are generally employed in the purification of proteins and peptides has the following chemical and physical characteristics:

| | | |
|---|---|---|
| (a) | Molecular weight: | 12400 (estimated by Bio-Gel P-30 gel filtration method) 12500 (by SDS-polyacrylamide gel electrophoresis method) |
| (b) | Appearance: | white amorphous powder; |
| (c) | Coloration reaction: | positive to ninhydrin and biuret reaction, negative to anthrone and Blix reaction; |
| (d) | Solubility: | soluble in water, insoluble in ethanol, acetone, propanol, butanol; |
| (e) | Ultraviolet spectrum: | as shown in FIG. 1; |
| (f) | Infrared spectrum: | as shown in FIG. 2; |
| (g) | Elemental analysis: | C: 46~47%, H: 6.0~7.0%, N: 12~13%; |
| (h) | Amino acid composition: | as shown in Table 5; |
| (i) | Isoelectric point: | 3.5 (estimated isoelectric point by electrophoresis method); |
| (j) | Antimicrobial activity | positive against *Bacillus subtilis* ATCC 6633, *Sarcina lutea* ATCC 9341 and *Streptococcus aureus* FDA 209 P; |
| (k) | Antitumor activity: | positive against mouse leukemia L 1210, P 388 and P 1534. |

AN-7D as characterized above may be classified as a high molecular antibiotic and differs from the known antibiotics shown in Table 1 by the characteristics shown in Table 2.

TABLE 2

| Antibiotics | differences in characteristics from AN-7D |
|---|---|
| Carcinocidin | insoluble in water, chromoprotein |
| Melanomycin | insoluble in water, chromoprotein |
| A-280 | chromoprotein |
| Iyomycin complex | insoluble in water at pH 2 to 4, chromoprotein |
| Plurallin | chromoprotein, M.W. is 30,000 to 60,000 |
| Actinoxanthin | amino acid composition, methionine is not present |
| Neocarzinostatin | M.W. is 10,700, amino acid composition |
| Macromomycin | amino acid composition, methionine and arginine are not present |
| Sporamycin | amino acid composition, histidine, arginine, methionine, cystein and proline are not present |

Of the known agents, NCS, is reported to have a notable antitumor activity against mouse leukemia L1210 and to exhibit a very high chemotherapeutic coefficient. Compared with NCS, AN-7D is capable of inhibiting the cell growth of mouse leukemia P1534 against which NCS is ineffective in an in vivo tumor screening system. AN-7D shows a greater life prolongation effect for mouse leukemia and its maximum life prolongation effect reaches 306.4%.

AN-7D can be determined by the bio-assay method using *Escherichia coli* MP-2 FERM-P5434 as described in Agric. Biol. Chem., 43, 371(1979), and 1.0 unit/ml of antimicrobial activity corresponds to 10.1 μg/ml of purified AN-7D.

AN-7D can be produced by culturing microorganisms belonging to the genus Streptomyces which are capable of producing AN-7D. For example, *Streptomyces griseoincarnatus* B19C (AJ 9421 FERM BP-129) can be cultured in a culture medium, and then AN-7D which accumulates can be isolated from the culture broth and purified. The strain identified above by the indicated FERM-BP number was originally deposited on June 6, 1981 at the Fermentation Research Institute, Agency of Industrial Science and Technology, Ministry of International Trade and Industry (FR1) 1-3, Higashi 1-chome, Yatobe-machi, Tsukuba-gum, Ibaragi-ken 305, Japan. This deposit was converted to a deposit under the Budapest Treaty on May 14, 1982 with FRI which has acquired the status of an International Depository Authority as of May 1, 1981.

The strain B19C has the same general characteristics as the known strain ATCC 23623, which characteristics are described in Int. J. Syst. Bact. 18:20 and 328 (1968). The microorganism identified above is cultured aerobically in a conventional culture medium containing carbon sources, nitrogen sources, inorganic ions, and when required, minor nutrient elements, preferably with the pH of the medium adjusted to 4 to 9 and the temperature at 25° to 38° C. for 1 to 5 days.

Suitable carbon sources include starch, saccharides such as glucose, fructose, maltose, rhamnose, xylose, lactose, sucrose, and molasses and hydrolyzed starch containing these saccharides; organic acids such as acetic acid; and alcohols such as ethanol, and glycerol, which are preferably used. Suitable nitrogen sources include, for example, ammonium sulfate, gaseous ammonia, ammonia water, amino acids, hydrolyzed casein and yeast extract containing amino acids. Suitable inorganic ions include, for example, $K^+$, $PO_4^{---}$, $Ca^{++}$, $Mg^{++}$, $Cu^{++}$, $Zn^{++}$, $Mn^{++}$ and $Fe^{++}$. AN-7D produced in the culture broth can be isolated from the culture broth and purified by a series of entirely conventional purifying techniques such as by the salting out effect, dialysis, gel filtration, and ion-exchange chromatography, all of which have been employed in the purification of proteins and peptides.

Having generally described this invention, a further understanding of the invention can be obtained by reference to certain specific examples, which are provided herein for purposes of illustration only and are not intended to be limiting unless otherwise specified.

EXAMPLE 1

Twenty ml portions of Culture Medium A having the composition shown in Table 3 were placed into 500 ml-flasks, which were then heated at 110° C. for 10 minutes for sterilization.

TABLE 3

| | Composition of Culture Medium | | |
|---|---|---|---|
| Component | Conc. | Medium A | Medium B |
| Glucose | (g/dl) | 1.0 | 3.0 |
| Soluble starch | " | 1.0 | — |
| Peptone | " | 0.5 | 0.5 |
| Dried Yeast | " | 0.5 | 0.5 |
| Bouillon | " | — | 0.5 |
| NaCl | " | 0.5 | 0.5 |
| $CaCl_2.2H_2O$ | " | 0.1 | 0.2 |
| $MnCl_2.4H_2O$ | (mg/dl) | 0.1 | 2.0 |
| $FeCl_2.6H_2O$ | " | 0.1 | — |
| pH | | 7.0 | 7.0 |

*Streptomyces griseoincarnatas* B19C (FERM BP-129) grown on bouillon agar slant, was inoculated into several batches of culture medium, and cultured with shaking at 30° C. for 24 hours to prepare seed culture broths. On the other hand, three hundred ml portions of Culture Medium B in Table 3 were placed into 1.0 liter-fermentation vessels and heated for sterilization. Each medium was inoculated with 20 ml of a seed culture broth described above and cultivation was conducted at 30° C. with agitation and aeration. After 50 hours of cultivation, the antibacterial activity of the resultant culture broth against *Escherichia coli* MP-2 was 16 units/ml, which corresponds to 162 μg/ml of purified AN-7D. A 1.0 liter culture broth thus obtained was centrifuged at a low temperature (0°-5° C.) at 8,000 rpm for 20 minutes to separate the microbial cells, and the supernatant was then saturated to 80% with ammonium sulfate. After adjusting the pH to 3.2 with 6N-acetic acid solution, the solution was allowed to stand at 5° C. for 30 minutes, thereby precipitating AN-7D together with other high molecular weight impurities from the ammonium sulfate solution. Then the precipitate was collected by centrifugation (10,000 rpm for 20 minutes) and dissolved into 100 ml of deionized water. The resulting solution was placed into cellophane bags and dialyzed against 0.02M phosphate buffer (pH 7.0) at 5° C. for 24 hours. Then the dialyzate was centrifuged (8,000 rpm) at 5° C. for 10 minutes to remove impurities which precipitated during the dialysis. Thereafter, 40 ml of DEAE-cellulose DE-52 was added to the supernatant solution, which was stirred in an ice bath for 30 minutes. The mixture was filtered through filter paper and the filtrate, the pH of which was adjusted to 5.0 with 2N-acetic acid, was dialyzed at 5° C. against 0.002M phosphate buffer (pH 7.0) for 24 hours and applied to a column of DEAE-cellulose DE-52 (1.6×40 cm) equilibrated with 0.002M phosphate buffer (pH 7.2). This column was washed with a sufficient volume of the equilibration buffer, and then eluted with the same buffer containing 0.2M sodium chloride. Fractions with the antibacterial activity were collected and lyophilized to obtain 40.5 mg white powder. The active fractions after DEAE-cellulose chromatography were submitted to gel filtration on a column of Bio-Gel P-30 (1.6×40 cm) using 0.002M phosphate buffer containing 0.1M sodium chloride as a solvent at a flow rate of 1.0 mg/5 min. The effluents having antibacterial activity were collected, dialyzed against deionized water at 5° C. for 48 hours and lyophilized, thereby yielding 20 mg AN-7D in the form of a white powder. The AN-7D thus purified had 6225 units/mg of antibacterial activity to *E. coli* MP-2 and was identified to be homogeneous both by Bio-Gel P-30 gel filtration and polyacrylamide gel electrophoresis.

The chemical and physical characteristics of the thus purified AN-7D were determined and the results are as follows:

(a) Molecular weight:
  12400 (estimated by gel filtration)
  12500 (by SDS-polyacrylamide gel electrophoresis)

In the estimation of molecular weight by the gel filtration method, the sample was submitted to gel filtration on a column of Bio-Gel P-30 (1.6×20 cm) using 0.02M phosphate buffer (pH 7.2) containing 0.1M sodium chloride as a solvent with a flow rate of 3.0 ml/5 min. and the molecular weight was estimated from the reference curve of the standard molecular weight markers.

Another estimation of the molecular weight was performed by SDS-polyacrylamide gel selectrophoresis using 30% polyacrylamide gel according to the method of Weber et al as described in J. Biol. Chem., Vol. 1, 244, 16, 4406 (1969)

(b) Coloration reaction: as shown in Table 4

TABLE 4

| Coloration reaction | |
|---|---|
| Reaction | Result |
| ninhydrin reaction | + |
| biuret reaction | + |
| anthrone reaction | − |
| Blix reaction* | − |

*In the pretreatment, a sample was hydrolyzed with 4N—HCl at 100° C. for 4 hours to liberate hexosamine.

(c) Ultraviolet spectrum: as shown in FIG. 1.
(d) Amino acid composition: as shown in Table 5.

TABLE 5

| Amino Acid Composition | | | |
|---|---|---|---|
| Amino Acid | % | Amino Acid | % |
| Asp | 12.0 | Cys at least | 1.5 |
| Thr | 10.1 | Ile | 2.2 |
| Ser | 7.2 | Leu | 6.6 |
| Glu | 7.1 | Tyr | 1.9 |
| Pro | 4.6 | Phe | 5.4 |
| Gly | 8.1 | Lys | 2.0 |
| Ala | 10.3 | His | 0.9 |
| Cys | —* | Trp | —* |
| Val | 8.1 | Arg | 4.0 |
| $NH_3$ | 7.8 | | |

*The content was not determined
The results shown in Table 5 were obtained from amino acid autoanalyzer (Model KLA5-B, Hitachi Seisakusho, Tokyo)

(e) Solubility: AN-7D is soluble in water but insoluble in ethanol, acetone, butanol and propanol.
(f) Infrared spectrum: as shown in Table 2.
(g) Elemental analysis: C: 46~47%, H: 6.0~7.0%, N: 12~13% S: 1-2%, O: 30–31%
(h) Isoelectric point: 3.5 (determined by an electrofocusing apparatus, Model SJ-1071, Atto Co. Inc., equipped with Servalyt Precotes)

In this experiment, the isoelectric points of ferritin, bovine albumin, and β-lactoglobulin were also determined as controls, and were found to be 4.4, 4.7 and 5.3, respectively.

(i) Antibacterial activity: as shown in Table 6.

TABLE 6

| Minimum Inhibition Concentration (MIC) of AN-7D | | |
|---|---|---|
| | MIC (μg/ml) | |
| Test Strain | AN-7D | Neocarzinostatin |
| Escherichia coli K-12 ATCC 10798 | >100 | >100 |
| Escherichia coli MP-2 | 4 | 2 |
| Bacillus subtilis ATCC 6633 | 3 | 15 |
| Sarcina lutia ATCC 93412 | 1 | 2 |
| Pseudomonas aeruginosa ATCC 10145 | >100 | >100 |
| Staphylococcus aureus FDA 209 P | 20 | 10 |

MIC in Table 6 were determined by the following procedure color:

Two ml portions of $M_3$-Medium (Bactoantibiotic Medium—Difico, 1.75%, pH 7.2) were placed into test tubes and heated at 120° C. for 10 minutes. Each test strain in Table 6 was inoculated into a batch of culture medium, and the inoculated media were cultured with shaking at 30° C. for 20 hours to obtain seed culture broths. A 0.05 ml sample of each culture broth was inoculated into 20 ml of $M_3$-Medium containing AN-7D or NCS. The inoculates were cultured at 37° C. for 20 hours with shaking. Thereafter, the optical density of each resultant culture broth at 660 nm was determined, and the MIC of each broth was calculated.

(j) Antitumor activity: as shown in Table 7.

TABLE 7

| Degree of multiplication of L1210 cells (%) | | |
|---|---|---|
| Concentration (μg/ml) | AN-7D | NCS |
| 0 | 100 | 100 |
| 0.05 | 100 | 100 |
| 0.10 | 100 | 100 |
| 0.20 | 100 | 100 |
| 0.30 | 0 | 85 |
| 0.50 | 0 | 20 |
| 1.00 | 0 | 0 |

The results presented in Table 7 were obtained by the following procedure. A 10.38 g sample of RPMI 1640 medium (Moore, G. E. et al, J. Nat Cancer Inst., 36, 405 (1966), Flow Laboratories, Inc. U.S.A.) was dissolved into 1.0 liter distilled water and 1.0 g $NaHCO_3$ was added to it. Then the solution was filtered through a Millipore filter (pore size: 0.22μ) and supplemented with 100 ml of germ-free blood serum. One ml portions of the culture medium thus prepared were placed into Falcon 3047 24-well Multi Well (Becton Dickinson & Co.) aseptically. Then a 0.05 ml culture sample of mouse leukemia L 1210 cells previously cultured was inoculated into each batch of the culture medium, and a definite amount of purified AN-7D or NCS dissolved in the same medium was added simultaneously to the culture medium. Thereafter, the inoculated media were incubated in a $CO_2$ gas incubator (concentration of $CO_2$ gas: 7.0%) at 30° C. After 5 days incubation, the numbers of multiplied cells were counted under a microscope and the relative multiplication numbers obtained are shown in Table 7.

EXAMPLE 2

One×$10^5$ mouse leukemia L 1210 cells were transplanted intrapertioneally into BDF, female mice bred for 5 weeks.

From the next day after transplantation of the tumor cells, 0.1~39 mg/kg/day of purified AN-7D were administered intrapertioneally for 5 days, and the average survival days were determined, from which life prolongation effects were calculated.

In a similar manner, life prolongation effects of commercial NCS were determined and these results are also shown in Table 8.

TABLE 8

| Amount Administered (mg/kg) | AN-7D A.S.D.* | AN-7D L.P.E.** | NCS A.S.D. | NCS L.P.E. |
|---|---|---|---|---|
| 0(control) | 9.4 ± 0.5 | 100 | 9.4 ± 0.5 | 100 |
| 0.1 | | | 13.4 ± 1.8 | 142.6 |
| 0.25 | | | 14.2 ± 2.9 | 151.1 |
| 0.63 | | | 9.2 ± 0.4 | 97.9 |
| 1.0 | 10.6 ± 1.1 | 112.8 | | |
| 1.56 | | | 7.2 ± 0.4 | 76.6 |
| 2.5 | 14.0 ± 4.1 | 148.9 | | |
| 6.3 | 15.0 ± 2.2 | 159.6 | | |
| 15.6 | 16.8 ± 5.9 | 178.7 | | |
| 39 | 28.8 ± 15.3 | 306.4 | | |

*Average survival days
**Life prolongation effect

EXAMPLE 3

One × 10$^6$ mouse leukemia P 388 cells were transplanted intraperitoneally into BDF, female mice bred for 9 weeks. Then 10 and 20 mg/kg/day of purified AN-7D were administered to the mice for 5 days intrapertioneally. In a similar manner, 1 × 10$^5$ mouse leukemia P 1534 cells were transplanted into BDF mice. From the next day after transplantation of the tumor cells 10 and 25 mg/kg/day of the purified AN-7D were administered to the mice for 5 days intraperitoneally. Then life prolongation effect was calculated from the average survival days of the test groups and the results obtained are shown in Table 9 and Table 10.

TABLE 9

Life Prolongation Effect on Mouse Leukemia P 388 Cells

| Amount of AN-7D Administered (mg/kg) | Average Survival Days | Life Prolongation effect (%) |
|---|---|---|
| none | 10.4 ± 2.1 | 100 |
| 10 | 15.6 ± 3.0 | 150 |

TABLE 9-continued

Life Prolongation Effect on Mouse Leukemia P 388 Cells

| Amount of AN-7D Administered (mg/kg) | Average Survival Days | Life Prolongation effect (%) |
|---|---|---|
| 25 | 14.0 ± 0 | 134 |

TABLE 10

Life Prolongation Effect on Mice Leukemia P 1534 Cells

| Amount of AN-7D Administered | Average Survival Days | Life Prolongation effect (%) |
|---|---|---|
| none | 11.2 ± 2.6 | 100 |
| 25 | 18.4 ± 5.7 | 164.3* |

*Significantly different to control ($P < 0.05$).

As shown in Table 10, the administration of An-7D can prolong the lives of the P 1534 bearing mice significantly.

In a similar manner, a 0.25 mg/kg/day amount of NCS was administered, but the life prolongation effect obtained was as low as 75%.

Having now fully described this invention, it will be apparent to one of ordinary skill in the art that many changes and modifications can be made thereto without departing from the spirit or scope of the invention as set forth herein.

What is claimed as new and desired to be secured by Letters Patent of the United States is:

1. A high molecular weight antibiotic AN-7D having the following characteristics:
   (a) molecular weight: 12400~12500: (by gel-filtration and SDS-polyacrylamide gel electrophoresis methods);
   (b) appearance: white amorphous powder;
   (c) coloration reaction: positive to ninhydrin and biuret reaction, negative to anthrone and Blix reaction;
   (d) solubility: soluble in water, insoluble in ethanol, acetone, propanol and butanol;
   (e) ultraviolet spectrum: as shown in FIG. 1;
   (f) infrared spectrum: as shown in FIG. 2;
   (g) elemental analysis: C: 46~47%, H: 6.0~7.0% S: 1-2%, O: 30-31%, N: 12~13%;
   (h) amino acid composition: as shown in Table 5;
   (i) isoelectric point: 3.5 (by isoelectric point electrophoresis)
   (j) antimicrobial activity: positive against
      *Bacillus subtilis* ATCC 663,
      *Sarcina lutea* ATCC 9341 and
      *Streptococcus aureus* FDA 209 P;
   (k) antitumor activity: positive against mouse leukemia cells L 1210, P 388 and P 1534.

* * * * *